United States Patent [19]

Barbe Frejaville et al.

[11] Patent Number: 5,750,710

[45] Date of Patent: May 12, 1998

[54] NITRONES WHICH ARE USABLE FOR THE SCAVENGING OF FREE RADICALS

[75] Inventors: Claudine Marie Clemence Barbe Frejaville, Aix En Provence; Hakim Karoui; Francois Le Moigne, both of Marseille; Marcel Culcasi; Sylvia Pietri, both of Montpellier; Paul Tordo, Marseille, all of France

[73] Assignee: Centre National de la Recherche Scientifique (C.N.R.S.), Paris, France

[21] Appl. No.: 403,783

[22] PCT Filed: Jul. 20, 1994

[86] PCT No.: PCT/FR94/00909

§ 371 Date: Mar. 16, 1995

§ 102(e) Date: Mar. 16, 1995

[87] PCT Pub. No.: WO95/03314

PCT Pub. Date: Feb. 2, 1995

[30] Foreign Application Priority Data

Jul. 20, 1993 [FR] France .................. 93/08906

[51] Int. Cl.$^6$ .................. C07F 9/141
[52] U.S. Cl. .................. 548/111; 548/119
[58] Field of Search .................. 514/461, 471; 548/412, 413, 543, 544, 111, 119; 424/9–33; 436/173

[56] References Cited

U.S. PATENT DOCUMENTS 4,099,918  7/1978  Keana .................. 23/230 R

FOREIGN PATENT DOCUMENTS 2 126 954  12/1971  Germany.
2 225 015  5/1990  United Kingdom.

OTHER PUBLICATIONS

Mercier A., B–Phosphonylated Five membered ring nitroxide. . . ., Tetrahedron Letters, (32)19, pp. 2125–2128, (1991).

Alberti A. et al, Spin Trapping of Radicals . . . ., Gazzetta Chimica Italiana, (113) pp. 869–871, (1983).

Primary Examiner—John M. Ford
Attorney, Agent, or Firm—Young & Thompson

[57] ABSTRACT

New nitrones which are usable for the scavaging of free radicals, are selected from 5-diethoxyphosphoryl-5-methyl-1-pyrroline 1-oxide, 5-phosphono-5-methyl-1-pyrroline 1-oxide, and 5-diethoxyphosphoryl-5-methyl-(2,3,3-$^2$H$_3$)-1-pyrroline 1-oxide, as well as its corresponding physiologically acceptable salts obtained by the action of an inorganic or organic base.

4 Claims, No Drawings

NITRONES WHICH ARE USABLE FOR THE SCAVENGING OF FREE RADICALS

BACKGROUND OF THE INVENTION

1. Field of the Invention

The present invention relates to cyclic nitrone derivatives which are usable as free-radical scavengers.

2. Description of the Related Art

A number of cyclic nitrones capable of scavenging free radicals are known at the present time: 5,5-dimethylpyrroline N-oxide (DMPO) is marketed in Europe by various companies such as Aldrich, Fluka and Sigma. This compound, a free-radical trapping agent, is used only in electron paramagnetic resonance experiments. Its application in the pharmaceutical and cosmetics fields is limited on account of its instability and its low solubility in biological media, as well as the instability of its scavenging adducts.

M. J. Turner and G. M. Rosen describe, moreover, in their paper published in J.Med. Chem. 29 (12), 2439-2444 (1986), three cyclic nitrones which proved to be more effective free-radical scavengers than DMPO, namely 5-butyl-5-methyl-1-pyrroline 1-oxide (BMPO), 5,5-dipropyl-1-pyrroline 1-oxide (DPPO) and 2-aza-2-cyclopentenespirocyclopentane 2-oxide (CPPO). However, the solubility of these compounds in biological media is insufficient as the result of their lipophilic properties, which are greatly superior to those of DMPO.

SUMMARY OF THE INVENTION

New cyclic nitrones displaying great stability and better solubility in biological media, and which lead to the formation of comparatively more stable scavenging adducts, have now been discovered.

The subject of the invention is cyclic nitrones of general formula I:

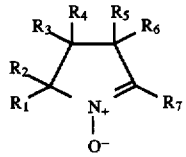

I in which:

$R_1$ represents a phenyl or alternatively a $(C_1-C_{18})$ alkyl, $R_2$ represents a hydrogen or deuterium atom, a phenyl or $(C_1-C_{18})$ alkyl group or a radical Z of formula

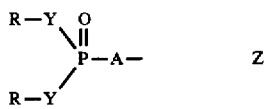

in which:

A is a single bond, a methylene group or an oxamethylene group (in which the oxygen atom is linked to the phosphorus atom of the radical Z), Y represents an oxygen atom and R represents a hydrogen atom, a $(C_1-C_{18})$ alkyl or a $(C_6-C_{18})$ aryl, or alternatively Y represents a methylene group and R represents a hydrogen atom, a $(C_1-C_{17})$ alkyl or a $(C_6-C_{18})$ aryl, $R_3$, $R_4$ and $R_5$ represent, independently of one another, a hydrogen or deuterium atom or a phenyl or $(C_1-C_{18})$ alkyl group, and $R_6$ represents a hydrogen or deuterium atom, a phenyl or $(C_1-C_{18})$ alkyl group or a radical

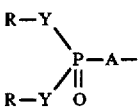

A representing a single bond and Y and R being as defined above, $R_7$ represents a hydrogen or deuterium atom or a methyl group, with the proviso that one and only one of the groups $R_2$ and $R_6$ represents the radical Z of formula

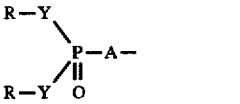

A representing a single bond, a methylene group or an oxamethylene group (in which the oxygen atom is linked to the phosphorus atom of the radical Z), and R and Y being as defined above, as well as their corresponding physiologically acceptable salts obtained by the action of an inorganic or organic base.

DETAILED DESCRIPTION OF THE PREFERRED EMBODIMENT

A preferred group of compounds of formula I consists of the compounds of the following formula II:

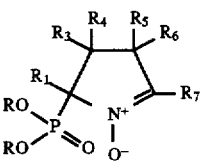

II in which:

R represents a hydrogen atom, a $(C_1-C_{18})$ alkyl or a $(C_6-C_{18})$ aryl, $R_1$ represents a phenyl or alternatively a $(C_1-C_{18})$ alkyl, $R_3$, $R_4$, $R_5$ and $R_6$ represent, independently of one another, a hydrogen or deuterium atom, a phenyl group or a $(C_1-C_{18})$ alkyl, and $R_7$ represents a hydrogen or deuterium atom or a methyl group.

Advantageously, $R_1$ represents a methyl group and $R_7$ is a hydrogen or deuterium atom.

Among these preferred compounds, the following may be mentioned 5-diethoxyphosphoryl-5-methyl-1-pyrroline 1-oxide (DEPMPO), 5-phosphono-5-methyl-1-pyrroline 1-oxide, and 5-diethoxyphosphoryl-5-methyl-(2,3,3-$^2H_3$)-1-pyrroline 1-oxide (DEPMPO$_D$).

$(C_1-C_{17})$ alkyl and $(C_1-C_{18})$ alkyl groups are understood to mean groups having a linear or branched chain possessing from 1 to 17 carbon atoms or from 1 to 18 carbon atoms, respectively.

$(C_6-C_{18})$ aryl group is understood to mean mono- or polycyclic aromatic compounds comprising from 6 to 18 carbon atoms.

The physiologically acceptable salts are those formed by the action of an inorganic or organic base on the compounds of formula I or II.

As preferred salts, the sodium salts of the phosphonic acids of formula I or II may be mentioned.

The compounds of the invention may be prepared by a process which consists in oxidizing by means of a suitable oxidizing agent a compound of general formula III:

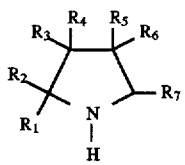

in which $R_1$, $R_2$, $R_3$, $R_4$, $R_5$, $R_6$ and $R_7$ are as defined above.

In this reaction, the oxidizing agent can advantageously be an organic peroxy acid such as m-chloroper-benzoic acid, an inorganic oxidizing agent such as sodium tungstate or alternatively any combination of inorganic oxide and hydrogen peroxide, such as selenium oxide in the presence of hydrogen peroxide, or, as a further alternative, an organic oxidizing agent such as dimethyl-dioxirane.

The reaction conditions depend on the nature of the oxidizing agent selected, and it is within the capability of a person skilled in the art to determine them using his basic general body of knowledge. Thus, when the oxidation takes place by the action of an organic peroxy acid, an inert solvent such as, for example, dichloromethane or chloroform will be chosen. When the oxidizing agent is hydrogen peroxide in aqueous solution in the presence of an inorganic oxide, the selection will fall on a polar aprotic solvent such as, for example, acetone.

The temperature can vary in accordance with the nature of the compound of formula III. It is advantageously between 0° C. and the refluxing temperature of the solvent.

The compounds of general formula III in which $R_2$ represents the radical

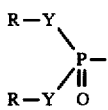

where R and Y are as defined above, may be prepared by a process which consists in reacting a halo ketone of general formula IV:

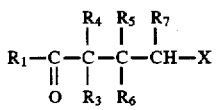

in which X represents a halogen such as chlorine, bromine or iodine, and $R_1$, $R_3$, $R_4$, $R_5$, $R_6$ and $R_7$ are as defined above, with the proviso that the group $R_6$ does not represent the radical

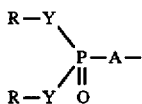

A representing a single bond and R and Y being as defined above, with a compound of formula V:

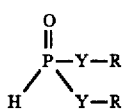

where Y and R have the same meaning as above, in the presence of $NH_3$.

Here too, the reaction conditions depend on the nature of the reactants of formula IV and V, and may be readily determined by a person skilled in the art. The reaction is generally conducted in a polar aprotic solvent. Advantageously, the solvent will be ethanol. The temperature may be between room temperature and the refluxing temperature of the solvent.

The compounds of formulae IV and V are commercially available compounds, or compounds which can be prepared by a person skilled in the art using known methods.

The compounds of general formula III in which $R_2$ represents a radical

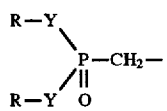

may be prepared by a process which consists in a) reacting the corresponding compound of formula VI

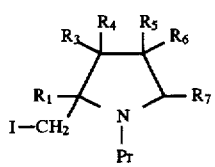

in which $R_2$, $R_3$, $R_4$, $R_5$, $R_6$ and $R_7$ are as defined above, with the proviso that the group $R_6$ does not represent the radical

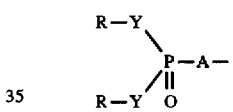

A representing a single bond and R and Y being as defined above, and Pr is a group protecting the amine function, such as, for example, a benzyloxycarbonyl group, with a phosphorus derivative of formula $P(YR)_3$, where Y and R are as defined above, b) and then deprotecting the secondary amine function by one of the methods known to a person skilled in the art.

The compounds of formula VI may be prepared in two steps from the following compounds of formula VIII

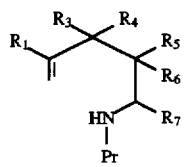

in which $R_1$, $R_3$, $R_4$, $R_5$, $R_6$, $R_7$ and Pr are as defined for the compound VI.

In a first step, a compound of formula VIII is reacted with mercury diacetate; the second step, which consists in treating the resulting product successively with potassium iodide and then iodine leads directly to the corresponding compound of formula VI.

The compounds of formula VIII are readily prepared by a person skilled in the art using known methods, from commercially available compounds.

The compounds of general formula III in which $R_2$ represents a radical

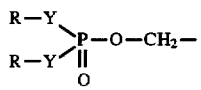

may be prepared by a process which consists in:

a) reacting the corresponding compound of formula

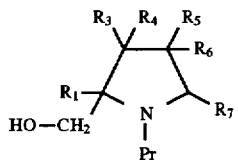

in which $R_1$, $R_3$, $R_4$, $R_5$, $R_6$, $R_7$ and Pr are as defined above, with the proviso that the group $R_6$ does not represent the radical

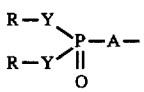

A representing a single bond and R and Y being as defined above, with a compound of formula X

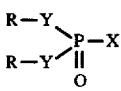      X in which X represents a halogen such as chlorine and R and Y are as defined above, b) and then deprotecting the secondary amine function by one of the methods known to a person skilled in the art.

The preparation of compounds of formula IX is carried out in two steps from the corresponding compounds of formula VIII:

in a first stage the compound of formula VIII is reacted with a mercury diacetate. In the second step, the resulting product is treated with oxygen in the presence of a hydride such as potassium borohydride to yield the expected compound of formula IX.

The preparation of the compounds of formula I in which $R_6$, represents a radical

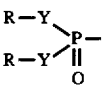

where R and Y are as defined above may be carried out in at least two different ways.

A first synthesis process consists in treating with sodium hydride the corresponding compound of formula XI

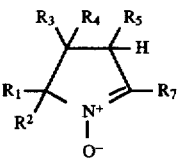      XI in which $R_1$, $R_2$, $R_3$, $R_4$, $R_5$, and $R_7$ are as defined above, with the proviso that $R_2$ does not represent a group

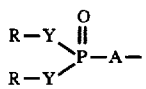

R and Y being as defined above and A representing a single bond, a methylene group or an oxamethylene group (in which the oxygen atom is linked to the phosphorus atom of the radical Z), and then in reacting the resulting sodium salt with a compound of formula X.

In the second synthesis process, a compound of formula XI is treated successively with N-bromo-succinimide and a compound of formula $P(YR)_3$ in which Y and R are as defined above. When the compound of formula I in question is such that Y is an oxygen atom, this reaction is known by the name of the Arbuzov reaction.

The compounds of formula XI are prepared by means of an oxidizing agent from the corresponding compounds of formula III. The method used has been explained in detail above.

The compounds of general formula I for which Y is an oxygen atom and R is a hydrogen atom may be obtained from the corresponding compounds of formula I in which R is an alkyl, by the action of a trimethylsilyl halide such as trimethylsilyl bromide under anhydrous conditions, followed by aqueous hydrolysis. In this reaction, an aprotic inert solvent may be used. Dichloromethane and chloroform may be mentioned as preferred solvents. The temperature depends on the compound of formula I in question, and may vary between room temperature and the refluxing temperature of the solvent.

The compounds of formula I for which one or more of the radicals chosen from $R_2$, $R_3$, $R_4$, $R_5$, $R_6$ and $R_7$ represent a deuterium atom are prepared from the compounds of the same formula in which the deuterium atoms are replaced by hydrogen atoms, by the action of sodium deuteroxide (NaOD) in heavy water ($D_2O$). The reaction temperature depends on the nature of the compound of formula I in question. Temperatures between 0° C. and the refluxing temperature of heavy water may be chosen with equal validity for this purpose.

The compounds of the invention are usable as free-radical scavengers. As such, and on account of their physicochemical properties, they find application in cosmetology and in the medical field.

In the human biological medium, several reactive oxygenated species, prooxidants of the $O_2^{-\cdot}$, $HO^{\cdot}$, $HOO^{\cdot}$ type, may formed from the oxygen transported in the body by respiration. In the normal situation, a low stationary concentration of these species is controlled by a series of enzymatic or non-enzymatic antioxidants which effect their removal.

A situation of oxidative stress becomes established when there is a local imbalance between antioxidants and prooxidants in favour of the latter. Situations of oxidative stress have been demonstrated in the case of various cardiovascular pathologies such as coronary ischaemia, arteriosclerosis and infarction, as well as in the case of extracorporeal circulation employed in vascular surgery or alternatively during inflammatory, infectious or cell aging processes.

The compounds according to the invention are effective free-radical scavengers which may be used in cosmetology as trapping agents of the prooxidant species responsible for cell aging.

In medicine, and more especially in the field of diagnosis, the compounds according to the invention are useful in the evaluation of oxidative stress. The direct detection of $O_2^{-\cdot}$, HOO·, HO· free radicals generated in vivo is not possible by electron paramagnetic resonance (EPR), in spite of their non-zero spin magnetism, as a result of their instability: these radicals possess, in effect, a half-life of the order of $10^{-5}$ to $10^{-3}$ second.

Spin trapping is the technique used for detecting these radicals. Its principle is as follows: the biological medium to be tested is placed in the presence of a free-radical scavenger S. If free radicals such as $O_2^{·-}$, HO·, HOO· are present in the medium, they combine with the scavenger S to form an adduct (S—$O_2$)·⁻, (S—OH)· or (S—OOH)·. This adduct is persistently paramagnetic, and can hence be detected by electron paramagnetic resonance (EPR).

With respect to free radicals, the compounds according to the invention have proved to be effective scavengers permitting the detection by EPR of prooxidant free radicals in biological media.

The use of the compounds according to the invention as free-radical trapping agents or scavengers affords many advantages. The stability of these compounds and their solubility in biological media may be mentioned.

The inventors have also been able to demonstrate that the kinetics of scavenging of free radicals such as HOO· by the compounds of the invention is very much faster than in the case of 5,5-dimethylpyrroline N-oxide (DMPO) of the prior art.

The reaction of trapping of the HOO· radical by DMPO is slow and characterized by a, second order rate constant k, of $10 M^{-1} s^{-1}$; the in vivo formation of the superoxide radical is consequently difficult to detect with DMPO. In contrast, the rate of trapping of the HOO· radical by 5-diethoxyphosphoryl-5-methyl-1-pyrroline 1-oxide (DEPMPO), a compound according to the invention, is 2.5 times as fast.

Moreover, during the detection of HOO· with DMPO, several authors have reported the decomposition of the (DMPO—OOH)· adduct to the (DMPO—OH)· adduct. This results in a poor reliability of spin trapping experiments carried out using DMPO.

On the other hand, in the case of DEPMPO, a compound according to the invention, no decomposition of the (DEPMPO—OOH)· adduct to the (DMPO—OH)· adduct has been observed.

The stability of the adducts obtained from the compounds according to the invention is further demonstrated by the following qualitative and quantitative experiments:

Freezing-thawing test

The possibility of storing blood samples taken from patients who are in various situations which may involve the existence of oxidative stress (in cardiovascular surgery with extracorporeal circulation, or in the case of myocardial infarction) is essential for the purpose of use in the medical field. In the case of the compounds according to the invention, the addition of the scavenging radical may be carried out before freezing and storage of the blood samples at 77 K as a result of the great stability of the scavenging adducts, as the following experiment shows:

The scavenging adducts of DEPMPO and the $O_2^{·-}$ and HOO· radicals were analysed by electron paramagnetic resonance after storage at 77 K and thawing. Their spectrum proved identical to that of the adducts before freezing, thereby demonstrating their good stability.

On the other hand, the same experiment using DMPO adducts lead to the appearance of many spurious signals interfering with the interpretation of the EPR spectra of the thawed adducts.

Kinetic study of the decomposition of nitrone-($O_2^{·-}$/HOO·) adducts

In this experiment, the radicals ($O_2^{·-}$/HOO·) were produced by irradiation in the visible in the presence of the riboflavin (0.1 mM)/DTPA (4 mM) system in 0.1M phosphate buffer (pH 7) at room temperature.

The nitrones studied are added to the irradiated solution at a concentration of 0.08M.

When irradiation is stopped, the production of ($O_2^{·-}$/HOO·) radicals ceases and the decrease in the [nitrones-($O_2^{·-}$/HOO·)] adducts is monitored by EPR analysis.

The variation of the concentration of adducts with time was studied in the case of the nitrones DMPO (of the prior art) and DEPMPO (of the invention). The values of the concentration of adducts were recorded after 2, 10, 20, 30 and 40 minutes. These values are shown in Table I.

TABLE I

| TIME (Minutes) | Concentration of (DMPO)-($O_2^{·-}$/HOO·) adducts | Concentration of (DEPMPO)-($O_2^{·-}$/HOO·) adducts |
| --- | --- | --- |
| 0 | 100 | 100 |
| 2 | 50 | 91 |
| 10 | 0 | 68 |
| 20 | 0 | 52 |
| 30 | 0 | 42 |
| 40 | 0 | 28 |

The kinetics of disappearance of the adducts are of the first order in both cases. The calculated rate constants are, respectively:

$k_{DMPO} = 1.4 \times 10^{-2} s^{-1}$ $K_{DEPMPO} = 1.4 \times 10^{-3} s^{-1}$

It emerges from the present study that the half-life of the [(DEPMPO)-(HOO·/$O_2^{·-}$)] adducts is ten times as large as that of the [(DMPO)-(HOO·/$O_2^{·-}$)] adducts.

The subject of the invention is also a composition intended for use in cosmetology, containing as active ingredient a compound according to the invention: the products of general formula I are combined with excipients, fragrances and appropriate colorants to form, for example, aerosols, solutions, creams or ointments.

Another subject of the invention is a diagnostic product which is usable in the evaluation of oxidative stress, comprising a compound according to the invention.

The examples which follow illustrate the invention without implied limitation. In the nuclear magnetic resonance (NMR) data, the chemical shifts δ are expressed in ppm relative to TMS.

EXAMPLE 1

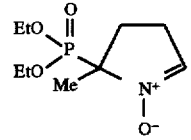

a) diethyl (2-methyl-2-pyrrolidinyl)phosphonate

A solution of 11.8 g of 5-chloro-2-pentanone and 14 g of diethyl phosphite in 50 ml of ethanol is maintained at 50° C. and under a stream of ammonia for 4 hours. The reaction mixture is then filtered and the solvent evaporated off. The residue is taken up with 40 ml of 2N HCl solution and then extracted with methylene chloride (2×50 ml). The aqueous phase is neutralized by adding sodium bicarbonate and extracted with chloroform. This organic phase is dried over sodium sulphate. Evaporation of the solvent under reduced pressure yields 13.7 g of a colourless oil.

b) 5-diethoxyphosphoryl-5-methyl-1-pyrroline 1-oxide

A solution of 4.4 g of 70% m-chloroperbenzoic acid in 40 ml of chloroform is added dropwise to a solution, cooled to 0° C., of 2 g of the above pyrrolidine in 30 ml of chloroform. The reaction mixture is then washed with saturated sodium bicarbonate solution (2×15 ml) and then with saturated sodium chloride solution (15 ml). The organic phase is dried over sodium sulphate and then concentrated under reduced pressure. The residue is chromatographed (silica, CH₂Cl₂/ EtOH 85:15) and gives 0.4 g of a yellow oil.

EXAMPLE 2

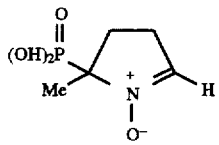

0.67 ml of trimethylsilyl bromide is added to 300 mg of 5-diethoxyphosphoryl-5-methyl-1-pyrroline 1-oxide dissolved in 5 ml of dry dichloromethane. The mixture is heated to reflux for 20 hours. The methylene chloride is evaporated off under reduced pressure. The residue is hydrolysed with 0.8 ml of water in 6 ml of acetone. The precipitate is filtered off, washed with acetone (15 ml) and recrystallized in dimethyl sulphoxide to give 137 mg of a white powder.

EXAMPLE 3

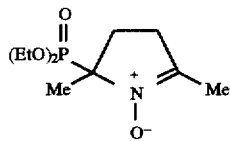

12.06 g of 30% aqueous hydrogen peroxide solution is added dropwise at 0° C. under argon to a solution of 8.61 g of 5-diethoxyphosphoryl-2,5-dimethyl-1-pyrrolidine and 0.21 g of SeO₂ in 72 ml of acetone. After the addition, the reaction mixture is left stirring at room temperature for 30 hours. The acetone is removed under reduced pressure. The aqueous phase is extracted with dichloromethane. The organic phase is dried over sodium sulphate and then concentrated under reduced pressure. The residue is chromatographed on a column (silica, CH₂Cl₂/EtOH 90:10) and yields 2.1 g of a yellow oil. EXAMPLE 4

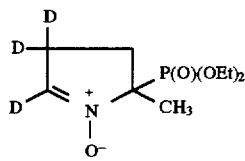

A solution of sodium deuteroxide (8N NaOD in D₂O, 0.2 ml) in 10 ml of heavy water, D₂O, cooled beforehand, is added slowly to a solution of 0.5 g of 5-diethoxyphosphoryl-5-methyl-1-pyrroline 1-oxide in 3 ml of heavy water, D₂O. The reaction is performed at room temperature under an inert atmosphere (argon) protected from light. The reaction is monitored by NMR. After 24 hours, the disappearance of the ethylenic proton signal is noted. The reaction medium is then extracted with dichloromethane (3×10 ml) which has been freshly distilled over phosphorus pentoxide (P₂O₅). The organic phase is then evaporated under reduced pressure. 0.3 g of a residual yellow oil is obtained.

We claim:
1. A compound of general formula I:

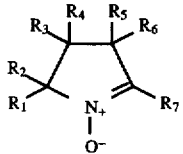

in which:

$R_1$ represents a phenyl or alternatively a $C_1$–$C_{18}$ alkyl, $R_2$ represents a hydrogen or deuterium atom, a phenyl or ($C_1$–$C_{18}$) alkyl group or a radical Z of formula

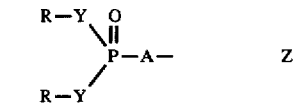

in which

A is a single bond, a methylene group of an oxamethylene group (in which the oxeygen atom is linked to the phosphorus atom of the radical Z), Y represents an oxygen atom and R represents a hydrogen atom, a ($C_1$–$C_{18}$) alkyl or a ($C_6$–$C_{18}$) aryl, or alternatively Y represents a methylene group and R represents a hydorgen atom, a ($C_1$–$C_{17}$) alkyl or a ($C_6$–$C_{18}$) aryl, $R_3$, $R_4$ and $R_5$ represent, independently of one another, a hydorgen or deuterium atom of a phenyl or ($C_1$–$C_{18}$) alkyl group, and $R_6$ represent a hydrogen or deuterium atom, a phenyl or ($C_1$–$C_{18}$) alkyl group of said radical Z $R_7$ representing a hydrogen or deuterium atom or a methyl group, with the proviso the one of the groups $R_2$ and $R_6$ must represent said radical Z, whereas the other of the groups $R_2$ and $R_6$ cannot represent said radical Z; as well as their corresponding physiologically acceptable salts obtained by the action of an inorganic or organic base.

2. Compounds according to claim 1, of formula II:

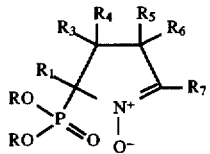

in which:

R represents a hydrogen atom, a ($C_1$–$C_{18}$) alkyl or a ($C_6$–$C_{18}$) aryl, $R_1$ represents a phenyl or alternatively a ($C_1$–$C_{18}$) alkyl, $R_3$, $R_4$, $R_5$ and $R_6$ represent, independently of one another, a hydrogen or deuterium atom or a phenyl or ($C_1$–$C_{18}$) alkyl group, and $R_7$ represents a hydrogen or deuterium atom or a methyl group.

3. Compounds of formula II according to claim 2, in which $R_1$ s a methyl group and $R_7$ is a hydrogen or deuterium atom.

4. Compound selected from:

5-diethoxyphosphoryl-5-methyl-1-pyrroline 1-oxide, 5-phosphono-5-methyl-1-pyrroline 1-oxide, and 5-diethoxyphosphoryl-5-methyl-(2,3,3-²H₃) -1-pyrroline 1-oxide, as well as its corresponding physiologically acceptable salts obtained by the action of an inorganic or organic base.

* * * * *